US010354342B2

(12) United States Patent
Kuper et al.

(10) Patent No.: US 10,354,342 B2
(45) Date of Patent: Jul. 16, 2019

(54) ADAPTIVE LIVESTOCK GROWTH MODELING USING MACHINE LEARNING APPROACHES TO PREDICT GROWTH AND RECOMMEND LIVESTOCK MANAGEMENT OPERATIONS AND ACTIVITIES

(71) Applicant: PERFORMANCE LIVESTOCK ANALYTICS, INC., St. Ansgar, IA (US)

(72) Inventors: Dane T. Kuper, St. Ansgar, IA (US); Dustin C. Balsley, Osage, IA (US); Thomas N. Blair, San Francisco, CA (US)

(73) Assignee: PERFORMANCE LIVESTOCK ANALYTICS, INC., St. Ansgar, IA (US)

( * ) Notice: Subject to any disclaimer, the term of this patent is extended or adjusted under 35 U.S.C. 154(b) by 0 days.

(21) Appl. No.: 15/996,432

(22) Filed: Jun. 2, 2018

(65) Prior Publication Data

US 2018/0350010 A1    Dec. 6, 2018

Related U.S. Application Data

(60) Provisional application No. 62/514,056, filed on Jun. 2, 2017.

(51) Int. Cl.
| | |
|---|---|
| G06Q 50/02 | (2012.01) |
| G06Q 10/06 | (2012.01) |
| G06N 7/00 | (2006.01) |
| A01K 29/00 | (2006.01) |
| G06N 20/00 | (2019.01) |

(52) U.S. Cl.
CPC ........... *G06Q 50/02* (2013.01); *A01K 29/005* (2013.01); *G06N 7/00* (2013.01); *G06N 20/00* (2019.01); *G06Q 10/0639* (2013.01)

(58) Field of Classification Search
None
See application file for complete search history.

(56) References Cited

U.S. PATENT DOCUMENTS

| | | | |
|---|---|---|---|
| 5,960,105 A | 9/1999 | Brethour | |
| 2005/0153317 A1* | 7/2005 | Denise | C12Q 1/6827 435/6.12 |
| 2006/0069023 A1* | 3/2006 | Alexander | A01K 67/0276 800/21 |
| 2007/0093965 A1* | 4/2007 | Harrison | A01K 29/005 702/19 |

(Continued)

FOREIGN PATENT DOCUMENTS

WO        0202822 A2    1/2002

*Primary Examiner* — Bijan Mapar
(74) *Attorney, Agent, or Firm* — Lazaris IP

(57) ABSTRACT

A method and system is provided in an adaptive framework for modeling livestock growth. The adaptive framework processes input data relative to livestock growth in an ensemble of one or more models and an artificial intelligence layer configured to select the most appropriate or primary model to optimize, predict, and recommend livestock feed operations based upon environmental, physiological, location and time variables within such input data. The adaptive framework also optimizes workflow by pen and by producer, based upon historical performance, gender and breed and the management practices of the producer.

30 Claims, 2 Drawing Sheets

(56) References Cited

U.S. PATENT DOCUMENTS

2009/0055243 A1* 2/2009 Lusk .................... C12Q 1/6888
 705/7.37
2012/0299731 A1 11/2012 Triener
2014/0088939 A1* 3/2014 Garant .................. G06Q 50/02
 703/2
2015/0359199 A1* 12/2015 Schaefer .............. A01K 29/005
 382/110

* cited by examiner ns and activities

CROSS-REFERENCE TO RELATED PATENT APPLICATION(S)

This patent application claims priority to U.S. provisional application 62/514,056, filed on Jun. 2, 2017, the contents of which are incorporated in their entirety herein. In accordance with 37 C.F.R. § 1.76, a claim of priority is included in an Application Data Sheet filed concurrently herewith.

FIELD OF THE INVENTION

The present invention relates to livestock management operations. Specifically, the present invention relates to an adaptive approach for modeling livestock growth based upon environmental, genetic, physiological requirements, location, facility type, financial considerations, and time variables to predict livestock growth rates and improve livestock feed and production operations.

BACKGROUND OF THE INVENTION

In the livestock industry, animal growth is the product of many different factors, many of which are constantly or frequently changing. Tracking and predicting animal growth for feedlot operations is a challenging endeavor for those involved in raising and feeding livestock, especially in the case of large commercial feedlots, because of the many variables involved.

There are several existing modeling approaches for livestock growth. These include net energy models for both maintenance and gain, which are commonly used to formulate diets for growing and finishing livestock such as cattle. These models focus on trying to predict the amount of energy used and the amount of feed to achieve energy requirements for maintenance and gain. Other existing models, such as total digestible nutrients (TDN), focus more on feed composition and need to be converted to net energy. Regardless, each model by itself suffers from limitations, and does not account for variables that may change across a single feedlot and which impact energy usage in a herd, such as real-time assessments of animal movement, feed consumption, environmental conditions, animal genetics, management practices, facility types, and herd and rangeland management practices.

BRIEF SUMMARY OF THE INVENTION

The present invention provides an adaptive framework that takes multiple inputs and variables into account in determining an average daily gain in modeling and predicting livestock growth. The adaptive framework is an application of machine learning methods to sets of unique models, each of which apply mathematical functions to optimize and predict livestock feed operations based upon environmental, genetic, physiological, location and time variables. The present invention also optimizes workflow by producer, by pen, and by animal, based upon historical performance, gender and breed, as well as the management practices of the producer, to analyze livestock performance. The adaptive framework generates recommendations from concurrently run livestock growth models that converge on the most appropriate livestock feedlot operations based on predictions of livestock growth.

It is one objective of the present invention to provide a system and method of modeling livestock growth rates using one or more machine learning approaches to optimize and predict feed operations. It is another objective of the present invention to provide a system and method of applying real-time assessments of environmental conditions and management practices to livestock growth models for predicting livestock growth rates and optimizing feeding operations. These assessments allow for ranking all available information impacting feeding operations to identify the products and practices that maximize livestock profitability.

It is still another objective of the present invention to combine location-tagged livestock data in farm operations with such real-time assessments of environmental conditions. It is another objective of the present invention to combine user-provided and/or observed feedback to present the current state of feed-related information based upon real-time assessments of location-specific conditions. It is yet another objective of the present invention to provide a diagnostic support tool that enhances decision-making in livestock operations.

There are many other specific objectives of the present invention. One such objective is to provide a system and method of providing predictive livestock feed recommendations for feed rations and animal feed additives. Nutritional additives include amino acids, enzymes, vitamins, minerals, antioxidants, acidifiers, binders, beta agonists, as well as the animal health products that that comprise ration mixtures. It is another such objective of the present invention to provide a system and method of recommending amounts and mixtures of feedstuffs based upon calculations performed within the present invention.

Other objects, embodiments, features, and advantages of the present invention will become apparent from the following description of the embodiments, which illustrate, by way of example, principles of the invention.

BRIEF DESCRIPTION OF THE SEVERAL VIEWS OF THE DRAWINGS

The accompanying drawings, which are incorporated in and constitute a part of this specification, illustrate several embodiments of the invention and together with the description, serve to explain the principles of the invention.

DETAILED DESCRIPTION OF THE INVENTION

In the following description of the present invention, reference is made to the exemplary embodiments illustrating the principles of the present invention and how it is practiced. Other embodiments will be utilized to practice the present invention and structural and functional changes will be made thereto without departing from the scope of the present invention.

The present invention is, as noted above, a system and method for utility in livestock management and feeding operations. In one aspect thereof, the present invention is an adaptive framework 100 for modeling and predicting livestock growth rates 172. The framework 100 contemplates that many different modeling approaches may be applied in the present invention, and such approaches may also be referred to herein as an ensemble growth model or livestock growth model generally, or as a convergence-based ensemble of adaptive livestock growth models 150. Regardless, the present invention enables improved accuracy in predicting livestock growth and rates of growth over time, predicts optimal feed-and veterinary related directives, and allows producers of livestock 104 to ensure that their animals get the diet, nutrition and health supplements needed to achieve a desired growth rate.

Figure 1:
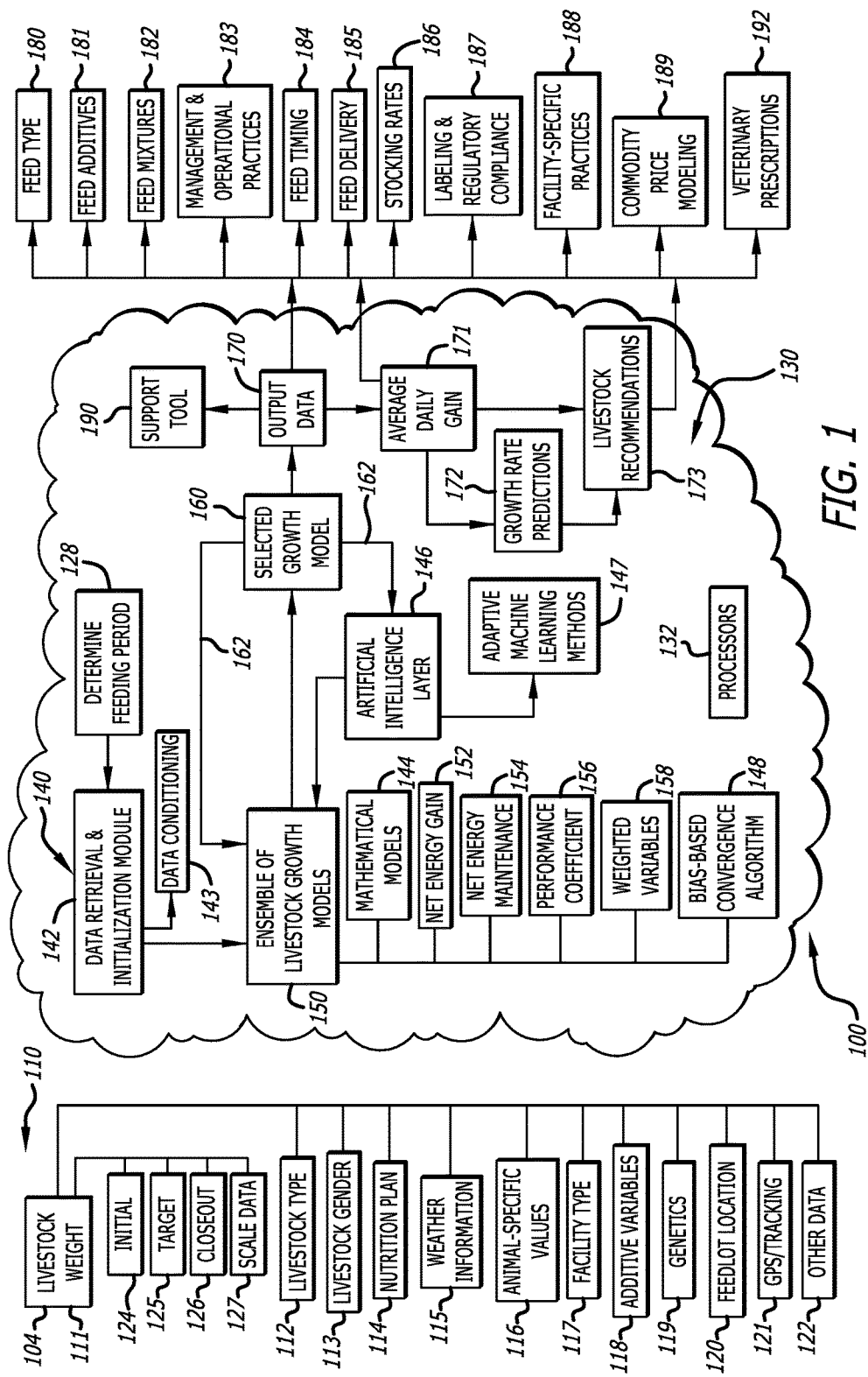
FIG. 1 is a system diagram illustrating components in an adaptive framework for modeling livestock growth rates according to one embodiment of the present invention.

FIG. 1 is a block diagram illustrating system components of the framework 100 for applying such a convergence-based ensemble of adaptive livestock growth models 150 to determine and predict a livestock growth rate 172 over time. The framework 100 applies a plurality of input data 110 to one or more models within the convergence-based ensemble of models 150. These livestock growth models 150 may be standardized models, and may also include one or more models customized according to proprietary formulas. Regardless, the framework 100 also includes at least one artificial intelligence layer 146 that enhances the convergence-based ensemble modeling 150 to select a particular and most appropriate model 160, and generate output data 170 such as an average daily gain 171 and recommendations 173 based on predictions of livestock growth rates 172.

The present invention identifies and assigns weights, or biases, to variables 158 represented in the various types of the input data 110 as described further herein. These variables 158 may be applied to a plurality of data processing components 140 within a computing environment 130 in which the systems and methods described herein are performed for analytical processing, such as applying one or more mathematical models 144 within the convergence-based ensemble of models 150. The computing environment 130 may include one or more processors 132 and a plurality of software and hardware components, and the one or more processors 132 and plurality of software and hardware components may be configured to execute program instructions or routines to perform the functions performed within the plurality of data processing components 140.

The data processing components 140 may include a data retrieval and initialization module 142, which is configured to ingest, receive, request, or otherwise obtain input data 110. This data retrieval and initialization module 142 may also be configured to condition or format 143 raw input data 110 so as to be prepared for the convergence-based ensemble of adaptive livestock growth models 150 and adaptive machine learning 147 and artificial intelligence 146 aspects of the framework 100. Such a module 142 (and its data conditioning features 143) takes raw input data 110 and formats it in ways that each independent algorithm of the ensemble of growth models 150 needs in order to operate correctly, such as CWT standardization, representations of various energy formats, etc.

The one or more mathematical models 144 include analyzing weight gain allowance from energy intake in a net energy gain model 162, where average daily gain is expressed as a function of net energy gain and weight. Net energy gain is measured in megacalories and determined by a formula for growing cattle energy requirement, based from a known NRC cattle growth calculation expressed at least in part as $(((0.077*wt^0.75)*type*gender*n_{emr})+p_{temp})$. As noted above, multiple types of input data 110 impact the calculations performed within these mathematical models 144.

The input data 110 for these mathematical models 144 and the livestock growth models 150 may include many different variables 158 that impact livestock growth rates over a livestock feeding period 128. For example, input data 110, and variables therein, for determining a growing cattle energy requirement for maintenance include weight 111, type 112, a body score calculation, and gender 113. Weight 111 may be expressed as kilograms (or pounds) of body weight, either current, shrunk, or live, and may also include an initial weight 124, a target weight 125, a closeout weight 126, and actual scale information 127. A type 112 of livestock 104 may also be included in the input data 110, and may be expressed by a value describing the relative utilization of energy for maintenance for the type 112 of livestock 104 being fed. Gender 113, in the case of cattle, may be represented by a value indicating the relative difference in maintenance energy requirements between classifications such as bulls, heifers, steers, and cows.

Net energy required for maintenance 154, or $n_{emr}$, is a modeling approach that produces a variable 158 representing an adjustment describing the effect of a previous plan of nutrition 114, and is calculated in a formula as at least in part a function of a body condition score reflected as either green (skinny), medium, or heavy (fat). The variable $p_{temp}$ 158 is also an adjustment and calculated in a formula that accounts for previous temperature or other weather information 115. The value used in based on the daily average temperature in degrees C., which is weather information 115 acquired or obtained using one or more real-time weather application programming interfaces (APIs) and using geo-location data 121 as noted further below.

In the present invention, the one or more mathematical models 144 include a performance coefficient 156, which is a maintenance ratio used during the feeding period 128, and is reflected by multiple variables used to calculate and predict animal growth. These include animal-specific values 116 such as coat insulation value, lower critical temperature, tissue insulation, hair depth, hide thickness, heat production, and external insulation. These variables also account for type of facility 117 in which the livestock 104 reside, and additive variables 118 such as their dry matter intake, calorie intake, implants, antibiotics, biological additives, beta agonists, and food sources, as well as genetics 119. Weather-specific information 115 in these variables includes wind speed, solar radiation, humidity, and soil conditions (such as for example soil temperature and moisture content at various depths) to compute a mud score, accounting for lots in which cattle stand in mud, requiring more energy for the livestock 104 to move or walk through mud, thereby increasing calorie usage.

Multiple livestock growth models 150 may be used in the adaptive framework 100 for predicting livestock growth rates 171 of the present invention. These sets of models 150 may be derived from existing, standardized models, and may also include models that incorporate unique bias traits based upon the variables 158 and the input data 110 discussed above.

The ensemble growth model approach 150 also incorporates adaptive machine learning methods 147 to predict and recommend livestock feed and management operation optimizations based upon environmental, physiological, genetic, location and time variables in the input data 110. The present invention optimizes workflow by animal, by facility, by pen, and by producer, based upon historical performance, gender and genetic breed and the management practices of the producer. The artificial intelligence-based modeling applied in the adaptive framework 100 calibrates the predictive recommendation unique to each producer, pen, and animal, to analyze livestock performance by location, weather, veterinary medicine or biological product, over time, by intra-organizational comparison, or benchmarks by gender, breed or by feed ration mix.

As noted above, in one embodiment of the present invention, the framework 100 incorporates a feedback loop 162 that enables validation of the selected growth model 160 and the predictions generated using such a model 160. The feedback loop 162 provides the convergence-based ensemble of livestock growth models 150 with actual closeout weight 126 and actual scale information 127, and is used to validate and correct growth model predictions to improve the selection of appropriate/primary models 160 in the ensemble-based approach 150. Therefore, the framework 100 of the present invention is built to improve its modeling performance and output recommendations 172 over time.

After selecting the most appropriate or primary model 160, one or more other models 150 may in some cases be selected to calculate a weight, bias, or offset which is dependent on inputs which are not considered by the primary model. For example, the primary model (as selected by the artificial intelligence layer 146 might use food consumption and breed to calculate a reasonably accurate weight, but not take weather and mud scores into account. A second model which uses weather inputs might be selected to calculate a reduction when the weather is cold or rainy, and a third model which uses mud scores might be selected to calculate an increase because of the location's favorable soil condition. In this way, the final output 170 may be tailored to the particular animal.

Models used in the multiple livestock growth models 150 may include, as noted above, net energy models such as net energy gain 152 and net energy required for maintenance 154. Other models may include total digestible nutrient models, and growth rate models based on particular types or components of feed rations such as those developed by the University of California at Davis. Multiple models are applied because no one model may account for variables that, for example, may change across a single feedlot and which impact energy usage in a herd. Therefore, multiple models that incorporate biases or weights assigned to variables 158 are used in the framework 100 to improve calculations of average daily gain 171 and growth rate predictions 172. Regardless, each livestock growth model 150 are used to predict future livestock weight and growth rates based upon a series of attributes characteristic of the livestock that are extrapolated from the various types of input data 110, and each model executes one or more algorithms to predict future livestock weight gain and growth rates, and the subsequent rationalization of actual versus predicted livestock performance. It is to be understood that the biases and weights assigned to each variable 158 in the input data 110 are assigned and derived based on the difference, or "delta", between actual and predicted performance, and it is this difference that determines the bias or weight assigned to each variable 158 for the next instantiation of each model 150. It is therefore to be further understood that one or more of the artificial intelligence layer 146, the adaptive machine learning components 147, the convergence algorithm 148, and the livestock growth models 150 themselves may evaluate the difference between actual performance data and predicted performance data, and return an instruction to the ensemble of livestock growth models 150 via the feedback loop 162 to adjust the biases and weights assigned to each variable 158 in execution of a livestock growth model 150, to arrive at a selected growth model 160 that most accurately calculates average daily gain 171 and predicts livestock growth rates 172 based on known livestock and other characteristics.

In addition to being related to the difference between actual and predicted performance, biases may also be calculated based on other attributes such as weather during a feeding period 128, and feed type used at various points during the feeding period 128. Biases may therefore be calculated adjusted based on cold weather growth, warm weather growth, a transition between cold and warm weather, and on feed type.

In one aspect of the present invention, the framework 100 may therefore compare predict performance data with actual closeout weight data 126, scale information 127, or any other indicator of livestock growth rate for adjusting these biases and weights assigned to variables 158. Additionally, this comparison may occur at any point during the feeding period 128, so that adjustments to the biases and weights assigned to each variable 158 may occur in real-time as a feeding period 128 changes over time.

Figure 2:
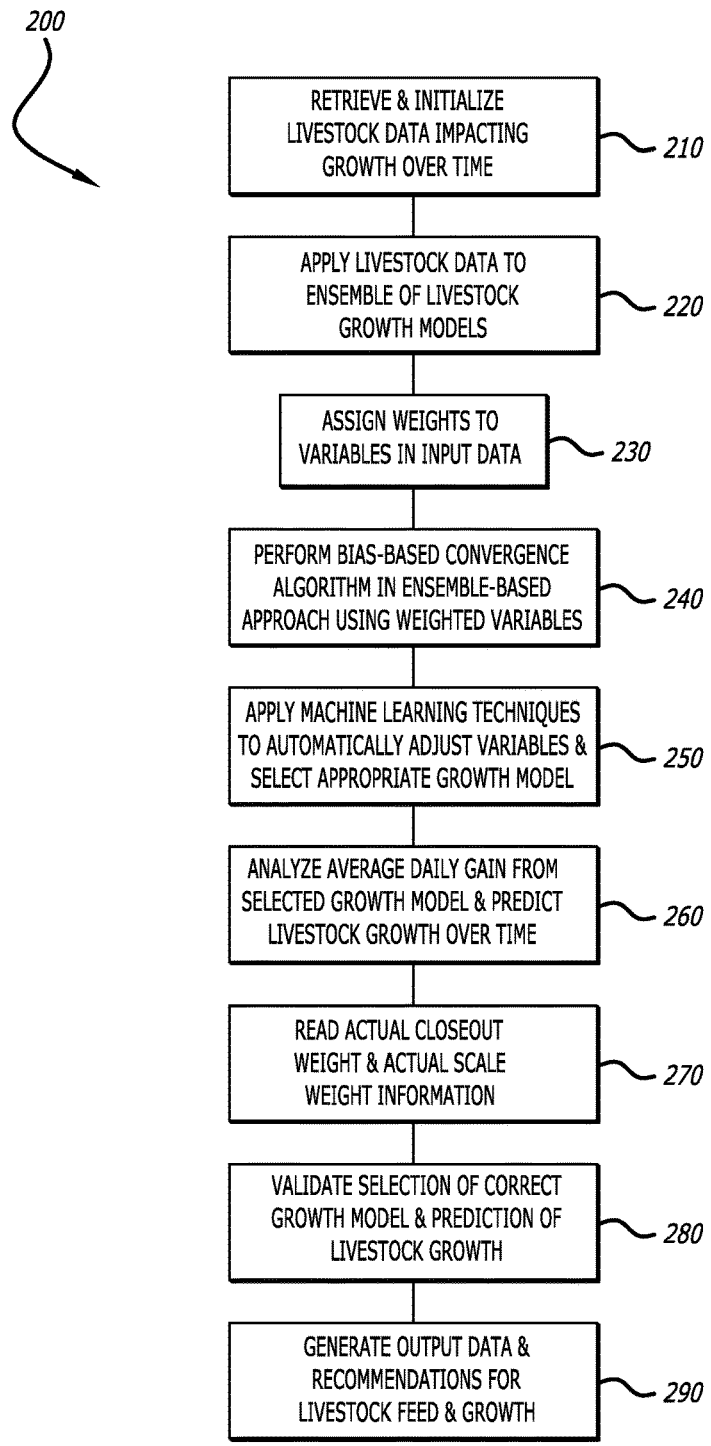
FIG. 2 is a flowchart of steps in a process of performing an adaptive framework for modeling livestock growth rates according to one embodiment of the present invention.

FIG. 2 is a flowchart illustrating a process 200 for performing the framework 100 of the present invention. The process 200 begins at step 210 by initializing and retrieving livestock information in the input data 110 that impacts growth rates over time. This information is then applied to the convergence-based ensemble of livestock growth models 150 at step 220. Processing of the input data 110 in the framework 100 then begins at step 230, with the identification of variables 158 and the assignment of weights to each variable 158 as discussed further herein.

A convergence algorithm 148 is then applied to the weighted variables 158 at step 240, which at least in part performs the bias-based approach in modeling the input data 110 in the ensemble of livestock growth models 150. The convergence algorithm 148 applies multiple mathematical models 144 within the livestock growth models 150 in this convergence-based, ensemble approach, so that multiple growth models 150 are applied at the same time to converge upon an average daily gain 171 to reach the target weight 125 that accurately predicts livestock growth rates over time. At step 250, the present invention applies additional machine learning techniques 147 in an artificial intelligence layer 146 to continually model the input data 110 using the convergence algorithm 148, and to automatically adjust the selected variables and assigned weights 158. The artificial intelligence layer 146 may also enable selection of a particular growth model 160 from the ensemble of livestock growth models 150 that most appropriately analyzes average daily gain 171 to achieve the target weight 125 during the feeding period 128.

At step 260, the framework 100 outputs the average daily gain 171 from the selected growth model 160 and uses this information to predict a livestock growth rate during the feeding period 128. At step 270, the framework 100 then reads the actual closeout weight 126 and actual scale information 127, and returns this additional weight data 111 in the feedback loop 162 to the convergence-based ensemble of livestock growth models 150, to confirm both the selection of the appropriate or primary model 160, and the prediction 173 of the livestock growth rate.

Returning to FIG. 1, as noted above, the adaptive framework 100 for modeling livestock growth is a multi-faceted approach that ingests appropriate input data 110, comprised of variables impacting livestock growth rates over time.

These are applied to multiple livestock growth models 150 (such as for example Net Energy Gain 162 and Net Energy Maintenance 164), which are configured to apply coefficients and perform mathematical functions to determine an average daily gain 171. The framework 100 also applies an artificial intelligence layer 146 and a convergence algorithm 158, to determine an ideal model 160 for predicting livestock growth rates 172. Finally, recommendations 173 are generated based on this prediction, and actual weight and scale measurements 126 and 127 are fed back into one or both of the artificial intelligence layer 146 and the convergence-based ensemble of models 150 to correct and improve future instantiations of the ensemble growth model 150, using the feedback loop 162.

As indicated in FIG. 1 and FIG. 2, the present invention utilizes multiple livestock growth models 150 for the various inputs 110 described herein. The present invention also utilizes adaptive machine learning techniques 147 to optimize, predict, and recommend livestock feed operations and management actions 173 based upon the environmental, physiological, location and time variables in the input data 110 analyzed using these multiple livestock growth models 150. These adaptive machine learning techniques 147 thereby form, in one aspect of the present invention, the artificial intelligence layer 146 on top of the multiple livestock growth models 150 that specifically calibrates each model based on different variables.

The artificial intelligence layer 146 may perform an ensemble-based processing step using the bias-based convergence algorithm 148 to run multiple, concurrent models 150 to determine the output of the ideal model 160 to promote. This multi-model, bias-based, ensemble processing approach promotes the most appropriate or primary livestock growth model 160 and resultant recommendations 173 such as feed program by selecting the most appropriate outcome and operational plan. This convergence approach may assign different weights or biases to different variables 158 among the input data 110, and the artificial intelligence layer 146 may apply one or more techniques to "learn" and adjust weights or biases to be applied based on historical correlations between modeled outcomes and the different variables, and based on the difference between actual growth rate performance and predicted growth rate performance. In a further configuration, the ensemble-based approach in the adaptive framework 100 of the present invention may select a particular maintenance ratio for a performance coefficient 156 by analyzing the multiple variables used to calculate and predict animal growth in the multi-model approach.

Actual performance data, for example from cattle producers, may also be used to determine if it either matches the predicted gain in the growth model(s), or result in a much different outcome than what the model(s) predicted. In general, this is due to differences in management practices and different characteristics in facilities 116. For example, if a producer has a facility 116 that is more comfortable for cattle, the animals will grow better. The artificial intelligence layer 146 registers differences experienced by producer, by pen, and by animal, and calibrates the ensemble of growth models 150 based on the specific cattle producer, and on each pen, or on each animal, at a specific producer at a particular facility 116.

As noted above, output data 170 in the present invention may be in the form of recommendations 173 based on predictions 172 of livestock growth generated by the ensemble approach and the adaptive artificial intelligence layer 146. Many types of recommendations 173 are contemplated, and may include for example recommendations 173 regarding a type of feed 180 to be provided to livestock (such as a type or variety of corn), recommendations as to type and quantity of additives 181 to feed (such as nutrients, antibiotics and veterinary medicines, biological additives, implants, and other animal health products, etc.), mixtures 182 of feed to be provided to livestock 104, and management practice and operational recommendations 183. Examples of management and operational practice recommendations 183 include feed timing 184, frequency of feed deliveries 185, stocking rates 186, labeling and regulatory compliance recommendations 187, facility-specific management practices 188, and veterinary prescriptions 192. Examples of facility-specific management practices 188 include cattle bedding rates, bunk space per head, and cattle movement and handling, such as moving livestock from one pen to another, or one location to another. Many other recommendations 173 are possible, and it is to be understood that the present invention is not to be limited to any specific recommendation 173 mentioned herein.

The ensemble approach incorporating the adaptive artificial intelligence layer 146 in the present invention may be applied to produce many further types of output data 170 in addition to those more directly related to optimizing and predicting livestock growth 172. As noted above, the present invention may be utilized to optimize and improve livestock management such as feed operations, for example by producing a more accurate understanding of various inputs attendant to such operations. This may include predicting real-time supply chain demand for essential feed elements, predicting a real-time demand for veterinary medicines, predicting a real-time demand for non-medicinal feed additives, and predicting real-time grain inputs for various types of feed. Another example of operational recommendations 183 based upon adaptive growth model projections includes the ability to recommend optimal timing for financial derivatives strategies including futures contracts and hedge strategies, in commodity price modeling 189. The ensemble approach may be used in each case to model such real-time inputs by region or by specific location, and by specific herd and type of animal, or for a particular animal, on a particular feedlot. Regardless, it is to be understood that the ensemble approach may be used to model may aspects of livestock growth and feedlot operations, and therefore the present invention is not to be limited to any specific use case discussed herein.

The output data 170 may be applied to a livestock management decision support tool 190 that is configured to allow users access to one or more automated processes for agricultural decision-making and recommendation writing. The decision support tool 190 also enables a user to input and/or select one or more of the variables, for example for defining various aspects of the mathematical models 144 performed within the performance beef growth model. The present invention may further include a component configured to generate output data 170 on a graphical user interface, for example on a computing device on which the decision support tool 190 is used to manage a feeding operation. Regardless, it is to be understood that one or more applications, mobile or otherwise, for enabling and working with the decision support tool 190 and with the present invention generally, may be accessed using a computer-based platform, such as for example on a desktop, laptop, or tablet computing device, or a mobile telephony device.

Models 150 may also be calibrated by variables that include real-time and historical weather and soil information. For example, the convergence-based ensemble of livestock growth models 150 may include one or more real-time weather application programming interfaces (APIs) for geo-referencing location-specific weather data 115. The present invention may utilize this location-specific weather data 115 in many ways. For example, weather information 115 may be used to adjust the coefficient daily gain calculation, based on daily forecast and actual weather information.

Models 150 may be further calibrated by variables that include real-time and historical soils information that reflect soil conditions at different strata throughout a growing season. For example, the convergence-based ensemble of livestock growth models 150 may include one or more application programming interfaces (APIs) for geo-referencing location-specific soils data, and similar to weather information 115, the present invention may utilize this location-specific soils data in many ways. For example, soils data, used to compute a "mud-score", may be used to adjust the coefficient daily gain calculation, based on daily soil temperature and moisture fluctuations that can affect mud depth and resistance, thereby increasing the energy required by the livestock 104 to move. This may also be based on both real-time field-level observations, or on forecasts or predictions of soil conditions for a specific location.

The present invention may also enable one or more additional and specific APIs to provide particular information or services and generate specific outcomes. APIs may be tailored to provide specific services, management actions, or information. Alternatively, services may be provided directly by the adaptive nature of the present invention. For example, the adaptive framework 100 may include an alerting module configured to generate alerts to livestock marketing organizations interested in when cattle will come of weight in the future, manufacturers of particular feed components interested in when medicine, additives and supplements should be re-ordered, nutritionists and veterinary visits scheduled, and buyers or auctioneers of livestock notified. It is to be understood that many types of alerting are possible within the present invention, and it is not to be limited to any one type of alert mentioned herein.

As noted above, actual performance data may be vastly different than predicted outcomes. In the ensemble growth models 150, livestock producers are able to enter a time and date for any time cattle are weighed, thereby providing an actual weight versus a forecast weight in the future. Closeout or scaled weights, and other actual measurements, are relayed back to the convergence-based ensemble of livestock growth model 150 to allow the framework 100 to learn and adapt from prior experience, exemplified by the actual weight data measured. The present invention serves to aggregate all predicted and observed weights from all sources to calibrate the convergence-based ensemble of growth model 150 over time.

The plurality of data processing components may be configured, as noted above, to perform the mathematical models 144 in the one or more existing livestock growth modeling paradigms using the various types of input data 110 as described herein. These data processing components 140 may apply the input data 110 to produce additional information as output data 170, for example for use as noted above by bankers, veterinarians, nutritionists, regulatory agencies, packers, and livestock marketing organizations.

As noted above, input data 110 may include feedlot location data 120. Feedlot location data 120 may be used in a number of ways, for example to correlate weather information 115 and other types of input data 110 to obtain the proper geographic location-specific information for the modeling paradigms 150 discussed herein.

Feedlot location data 120 may also may be used to provide additional recommendations 173 as output data 170 from the present invention. In one embodiment, the mathematical modeling functions 144 may correlate feedlot destination information with the nutritional content in collected ration weight information to model and predict growth rates in livestock 104 designated to consume such a feed ration on a specific feedlot.

Feedlot location data 120 may be correlated with Global Positioning System (GPS) and tracking data 121. Feedlot location data 120 may be represented in one or more GPS data points 121, and the framework 100 may include components such as a GPS-enabled receiver, which detects signals relative to the feedlot 120 and receives one or more GPS data points 121 to compute the feedlot's precise position on Earth. The GPS-enabled receiver may thereby extract and determine the geographical location of the feedlot 120 from the GPS data points 121.

Input data for the adaptive, ensemble-based framework 100 for livestock growth modeling of the present invention may also include one or more of livestock commodities data, such as live cattle, feeder cattle, corn, and hog future prices. This information may be used to develop a real-time understanding of livestock feeding information, which may be used to modify the ration mix, or to provide information necessary to make operational decisions such as determining which of the various additives, for example beta agonists, should be provided to the livestock 104 as feed in their ration mix.

The present invention, an adaptive, ensemble-based framework 100 for livestock growth modeling, is applicable to all types of livestock 104, and the modeling approach discussed herein may be adjusted depending on the type of livestock 104 being modeled. Accordingly, the present invention may also be styled as an ensemble swine growth model, an ensemble-based aqua-culture growth model, or to use the same bias-based convergence growth algorithm to optimize and predict the growth rate of poultry. The present invention is therefore not to be limited to any one type of livestock 104 mentioned herein.

The systems and methods of the present invention may be implemented in many different computing environments 130. For example, the convergence-based ensemble growth model 150 may be implemented in conjunction with a special purpose computer, a programmed microprocessor or microcontroller and peripheral integrated circuit element(s), an ASIC or other integrated circuit, a digital signal processor, electronic or logic circuitry such as discrete element circuit, a programmable logic device or gate array such as a PLD, PLA, FPGA, PAL, and any comparable means. In general, any means of implementing the methodology illustrated herein can be used to implement the various aspects of the present invention. Exemplary hardware that can be used for the present invention includes computers, handheld devices, telephones (e.g., cellular, Internet enabled, digital, analog, hybrids, and others), and other such hardware. Some of these devices include processors (e.g., a single or multiple microprocessors), memory, nonvolatile storage, input devices, and output devices. Furthermore, alternative software implementations including, but not limited to, distributed processing, parallel processing, or virtual machine processing can also be configured to perform the methods described herein.

The systems and methods of the present invention may also be partially implemented in software that can be stored on a storage medium, executed on programmed general-purpose computer with the cooperation of a controller and memory, a special purpose computer, a microprocessor, or the like. In these instances, the systems and methods of this invention can be implemented as a program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Additionally, the data processing functions disclosed herein may be performed by one or more program instructions stored in or executed by such memory, and further may be performed by one or more modules configured to carry out those program instructions. Modules are intended to refer to any known or later developed hardware, software, firmware, artificial intelligence, fuzzy logic, expert system or combination of hardware and software that is capable of performing the data processing functionality described herein.

The foregoing descriptions of embodiments of the present invention have been presented for the purposes of illustration and description. It is not intended to be exhaustive or to limit the invention to the precise forms disclosed. Accordingly, many alterations, modifications and variations are possible in light of the above teachings, may be made by those having ordinary skill in the art without departing from the spirit and scope of the invention. It is therefore intended that the scope of the invention be limited not by this detailed description. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a sub-combination or variation of a sub-combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what essentially incorporates the essential idea of the invention.

The invention claimed is:

1. A method, comprising:
   initializing and retrieving input data impacting a livestock growth rate over time, the input data at least including livestock weight data that includes an initial weight and a target weight, a livestock gender, a livestock type, a location, and a genetic breed;
   analyzing the input data in a plurality of data processing modules within a computing environment in which the plurality of data processing modules are executed in conjunction with at least one processor, the data processing modules configured to develop a model for continuously evaluating an average daily gain over time in a convergence-based ensemble of adaptive livestock growth models, by
      identifying a plurality of variables in the input data that are expected to impact the average daily gain over time, and assigning weights to the plurality of variables in the input data,
      calculating a performance coefficient representing a maintenance ratio during a livestock feeding period, the maintenance ratio based on weighted variables in the plurality of variables that are indicative of a body condition score for livestock as the livestock feeding period progresses,
      continuously performing the convergence-based ensemble of adaptive livestock growth models to analyze a weight gain allowance from energy intake and a growing cattle energy requirement for maintenance,
      selecting a particular livestock growth model from the convergence-based ensemble of adaptive livestock growth models to calculate the average daily gain to achieve the target weight over the livestock feeding period,
      predicting the livestock growth rate over time from the average daily gain,
      validating the selection of the particular livestock growth model, by returning an actual closeout weight and actual scale data to the convergence-based ensemble of the adaptive livestock growth models to confirm the predicted livestock growth rate, and
   initiating one or more management actions based on the predicted livestock growth rate and at least one of the livestock gender and the genetic breed, the one or more management actions including at least one of a sale of livestock, an adjustment of a rate of livestock feed, a delivery of a type of livestock feed, an application of a nutritional treatment to livestock, and a delivery of a veterinary treatment to livestock.

2. The method of claim 1, wherein the input data includes historical and current weather information, and further includes one or more of temperature, precipitation, wind speed, solar radiation, and humidity throughout the livestock feeding period.

3. The method of claim 1, wherein the input data further comprises a nutrition plan, a facility type, and a feedlot location.

4. The method of claim 3, further comprising obtaining a feedlot location from processing one or more GPS data points representing geographical coordinates associated with livestock with a GPS receiver, and determining the geographical coordinates of the feedlot location from the one or more GPS data points.

5. The method of claim 1, wherein the performance coefficient is further calculated from animal-specific variables influencing the body condition score, and that include one or more of coat insulation value, lower critical temperature, tissue insulation, hair depth, hide thickness, heat production, external insulation, dry matter intake, calorie intake, implants, antibiotics, biological additives, and food sources.

6. The method of claim 1, further comprising automatically adjusting the weights assigned to the plurality of variables as the livestock feeding period progresses.

7. The method of claim 1, wherein the convergence-based ensemble of adaptive livestock growth models include one or both of standardized models, and models customized according to particular formulas for analyzing the livestock growth rate.

8. The method of claim 1, wherein the convergence-based ensemble of adaptive livestock growth models include a net energy gain model.

9. The method of claim 1, wherein the convergence-based ensemble of adaptive livestock growth models include a net energy maintenance model.

10. The method of claim 1, further comprising calculating one or more additional weights, and assigning the one or more additional weights to variables for the input data that was not included in the convergence-based ensemble of adaptive livestock growth models for subsequent modeling of the average daily gain over time.

11. A system, comprising:
a data initialization component configured to retrieve input data impacting a livestock growth rate over time for a convergence-based ensemble of adaptive livestock growth models, the input data at least including a livestock weight that includes an initial weight and a target weight, a livestock gender, a livestock type, a location, and a genetic breed;
a plurality of data processing components configured to analyze the input data by developing a model for continuously evaluating an average daily gain in the convergence-based ensemble of livestock growth models by identifying a plurality of variables in the input data that are expected to impact the average daily gain over time, and assigning weights to the plurality of variables in the input data, and calculating a performance coefficient representing a maintenance ratio during a livestock feeding period, the maintenance ratio based on weighted variables in the plurality of variables that are indicative of a body condition score for livestock as the livestock feeding period progresses,
an artificial intelligence component configured to continuously perform the convergence-based ensemble of adaptive livestock growth models to analyze a weight gain allowance from energy intake and a growing cattle energy requirement for maintenance, select a particular livestock growth model from the convergence-based ensemble of adaptive livestock growth models, and predict the livestock growth rate over time from the average daily gain;
a feedback component configured to validate the selection of the particular livestock growth model by returning an actual closeout weight and actual scale data to the convergence-based ensemble of the adaptive livestock growth models to confirm the predicted livestock growth rate; and
an output data component configured to initiate one or more management actions based on the predicted livestock growth rate and at least one of the livestock gender and the genetic breed, the one or more management actions including at least one of a sale of livestock, an adjustment of a rate of livestock feed, a delivery of a type of livestock feed, an application of a nutritional treatment, to livestock, and a delivery of a veterinary treatment to livestock.

12. The system of claim 11, wherein the input data includes historical and current weather information, and further includes one or more of temperature, precipitation, wind speed, solar radiation, and humidity throughout the livestock feeding period.

13. The system of claim 11, wherein the input data further comprises a nutrition plan, a facility type, and a feedlot location.

14. The system of claim 13, wherein the plurality of data processing components are further configured to obtain a feedlot location from processing one or more GPS data points representing geographical coordinates associated with livestock with a GPS receiver, and determine the geographical coordinates of the feedlot location from the one or more GPS data points.

15. The system of claim 11, wherein the performance coefficient is further calculated from animal-specific variables influencing the body condition score, and that include one or more of coat insulation value, lower critical temperature, tissue insulation, hair depth, hide thickness, heat production, external insulation, dry matter intake, calorie intake, implants, antibiotics, biological additives, and food sources.

16. The system of claim 11, wherein the artificial intelligence component is further configured to automatically adjusting the weights assigned to the plurality of variables as the livestock feeding period progresses.

17. The system of claim 11, wherein the convergence-based ensemble of adaptive livestock growth models include one or both of standardized models, and models customized according to particular formulas for analyzing the livestock growth rate.

18. The system of claim 11, wherein the convergence-based ensemble of adaptive livestock growth models include a net energy gain model.

19. The system of claim 11, wherein the convergence-based ensemble of adaptive livestock growth models include a net energy maintenance model.

20. The system of claim 11, wherein the plurality of data processing components are further configured to calculate one or more additional weights, and assign the one or more additional weights to variables for the input data that was not included in the convergence-based ensemble of adaptive livestock growth models for subsequent modeling of the average daily gain over time.

21. A method, comprising:
determining an average daily gain in a plurality of data processing functions that perform a convergence-based ensemble of livestock growth models with input data that is expressed as a plurality of variables impacting livestock growth, the input data at least relative to a livestock weight that includes an initial weight and a target weight, a livestock gender, a livestock type, a location, and a genetic breed, by selecting a particular model in the convergence-based ensemble of livestock growth models, by assigning weights to the plurality of variables that are identified as having an impact on the average daily gain over time, calculating a body condition score for livestock as the livestock feeding period progresses, and a performance coefficient representing a maintenance ratio indicative of the body condition score, and continuously analyzing a weight gain allowance from energy intake and a growing cattle energy requirement for maintenance;

predicting a livestock growth rate based on the average daily gain from the selected particular model;

confirming the predicted livestock growth rate by returning an actual closeout weight and actual scale data to the convergence-based ensemble of the adaptive livestock growth models; and initiating one or more management actions based on the predicted livestock growth rate and at least one of the livestock gender and the genetic breed, the one or more management actions including at least one of a sale of livestock, an adjustment of a rate of livestock feed, a delivery of a type of livestock feed, an application of a nutritional treatment to livestock, and a delivery of a veterinary treatment to livestock.

22. The method of claim 21, wherein the input data includes historical and current weather information, and further includes one or more of temperature, precipitation, wind speed, solar radiation, and humidity throughout the livestock feeding period.

23. The method of claim 1, wherein the input data further comprises a nutrition plan, a facility type, and a feedlot location.

24. The method of claim 23, further comprising obtaining a feedlot location from processing one or more GPS data points representing geographical coordinates associated with livestock with a GPS receiver, and determining the geographical coordinates of the feedlot location from the one or more GPS data points.

25. The method of claim 21, wherein the performance coefficient is further calculated from animal-specific variables influencing the body condition score, and that include one or more of coat insulation value, lower critical temperature, tissue insulation, hair depth, hide thickness, heat production, external insulation, dry matter intake, calorie intake, implants, antibiotics, biological additives, and food sources.

26. The method of claim 21, further comprising automatically adjusting the weights assigned to the plurality of variables as the livestock feeding period progresses.

27. The method of claim 21, wherein the convergence-based ensemble of adaptive livestock growth models include one or both of standardized models, and models customized according to particular formulas for analyzing the livestock growth rate.

28. The method of claim 21, wherein the convergence-based ensemble of adaptive livestock growth models include a net energy gain model.

29. The method of claim 21, wherein the convergence-based ensemble of adaptive livestock growth models include a net energy maintenance model.

30. The method of claim 21, further comprising calculating one or more additional weights, and assigning the one or more additional weights to variables for the input data that was not included in the convergence-based ensemble of adaptive livestock growth models for subsequent modeling of the average daily gain over time.

* * * * *